US010690783B2

(12) United States Patent
Jewell et al.

(10) Patent No.: US 10,690,783 B2
(45) Date of Patent: Jun. 23, 2020

(54) RADON MEASUREMENT METHODS AND RADON MEASURMENT TOOLS

(71) Applicant: FORMATIVE HOLDINGS, LLC, Murray, UT (US)

(72) Inventors: Travis Allen Jewell, Sandy, UT (US); Jay Cranney, Sandy, UT (US)

(73) Assignee: FORMATIVE HOLDINGS, LLC, Murray, UT (US)

( * ) Notice: Subject to any disclaimer, the term of this patent is extended or adjusted under 35 U.S.C. 154(b) by 168 days.

(21) Appl. No.: 15/890,208

(22) Filed: Feb. 6, 2018

(65) Prior Publication Data

US 2018/0224562 A1  Aug. 9, 2018

Related U.S. Application Data

(60) Provisional application No. 62/455,889, filed on Feb. 7, 2017.

(51) Int. Cl.
*G01T 1/178* (2006.01)
*G01T 7/00* (2006.01)
*G01N 33/00* (2006.01)

(52) U.S. Cl.
CPC ......... *G01T 1/178* (2013.01); *G01N 33/0055* (2013.01); *G01T 7/00* (2013.01); *Y10S 250/02* (2013.01)

(58) Field of Classification Search
CPC .................................. G01T 1/178; G01T 7/00
See application file for complete search history.

(56) References Cited

U.S. PATENT DOCUMENTS 4,140,912 A * 2/1979 Bressan .................... G01T 7/04
250/394
4,269,059 A  5/1981 Baker
(Continued)

FOREIGN PATENT DOCUMENTS

WO  2016/005761  1/2016

OTHER PUBLICATIONS

International Search Report and Written Opinion dated Apr. 19, 2018, in related PCT Application No. PCT/US2018/017123.

*Primary Examiner* — David P Porta
*Assistant Examiner* — Jeremy S Valentiner
(74) *Attorney, Agent, or Firm* — Maschoff Brennan

(57) ABSTRACT

A radon measurement device includes a housing, a diffusion chamber, a diffusion chamber sensor, a diffusion pathway, a clock circuit, measurement circuitry, and a triggering mechanism. The diffusion chamber is disposed in an internal cavity of the housing. The housing includes a vent. The diffusion chamber sensor detects radioactive decay of radon and generates an electrical signal. The diffusion pathway enables introduction of ambient air into the diffusion chamber. The clock circuit outputs time data. The measurement circuitry receives the electrical signal and associates therewith a particular time datum. The triggering mechanism selectively isolates the vent from an environment and selectively triggers the measurement circuitry. Responsive to a triggering action on the triggering mechanism, the diffusion pathway is fluidly connected with the environment and functionality of the measurement circuitry is initiated. The detection data set is limited to a period between the triggering action and a particular measurement interval.

18 Claims, 10 Drawing Sheets

(56) References Cited

U.S. PATENT DOCUMENTS

| | | | | |
|---|---|---|---|---|
| 4,809,141 | A | * | 2/1989 | Leopoldi ................ B42D 5/007 |
| | | | | 362/208 |
| 4,871,914 | A | * | 10/1989 | Simon ..................... G01T 1/178 |
| | | | | 250/370.02 |
| 4,920,263 | A | * | 4/1990 | Fimian .................... G01T 1/003 |
| | | | | 250/253 |
| 5,093,570 | A | * | 3/1992 | Dorfi ........................ G01T 1/14 |
| | | | | 250/253 |
| 2002/0014596 | A1 | | 2/2002 | Harley et al. |
| 2004/0031928 | A1 | * | 2/2004 | Smith ..................... G01T 1/178 |
| | | | | 250/380 |
| 2004/0129890 | A1 | * | 7/2004 | Berman ................. G01T 1/178 |
| | | | | 250/380 |
| 2005/0010110 | A1 | | 1/2005 | Black et al. |
| 2009/0230305 | A1 | * | 9/2009 | Burke ..................... G01K 13/00 |
| | | | | 250/336.1 |
| 2012/0168882 | A1 | * | 7/2012 | Cherian ........... G01N 33/48785 |
| | | | | 257/414 |
| 2016/0299235 | A1 | | 10/2016 | Sundal et al. |

\* cited by examiner

RADON MEASUREMENT METHODS AND RADON MEASURMENT TOOLS

CROSS-REFERENCE TO RELATED APPLICATION

This application claims priority to and the benefit of U.S. Provisional Application No. 62/455,889, which is incorporated herein by reference in its entirety.

FIELD

The embodiments discussed in the present disclosure are related to radon measurement tools and methods of radon measurement. In particular, some embodiments relate to low cost, single calibration, single deployment, and electronic radon measurement tools and implementations thereof.

BACKGROUND

Radon gas is an invisible, odorless, naturally occurring radioactive gas that is created by the radioactive decay chain of Uranium. As Uranium decays, it becomes radium and radium decays to become radon gas. A form of radon gas, radon 222 gas, seeps out of the soil and into the atmosphere where it dilutes to a small percentage in the air. In this process, some of the radon gas enters homes and/or buildings via the foundation or by water that is present in the soil surrounding the foundation.

Radon gas is dangerous when inhaled into the lungs of individuals living and working in homes and/or buildings in which radon 222 has seeped. As inhaled radon gas decays, it becomes several other radon decay products that decay until becoming lead 206. Additionally, as radon decays, alpha radiation is released that can damage the tissue in lungs. Such damage can cause mutations that can eventually become cancerous. The health risks associated with Radon gas increase as the exposure amount increases and as a time of exposure increases.

Radon 222 gas in air is categorized as a group-1 carcinogen by the American Cancer Society. According to the United States Environmental Protection Agency (USEPA), radon 222 gas is the second leading cause of lung cancer causing greater than 20,000 deaths annually. The USEPA recommends that people take action to reduce exposure to radon levels greater than 4 picocuries per liter. The World Health Organization recommends that people take action or install a system to reduce exposure to radon gas levels greater than 2.7 picocuries per liter.

Radon gas occurs throughout the world in varying degrees. Although some areas are geologically less susceptible to radon gas, it can be a problem anywhere. Neighboring buildings can have radon levels of significant difference due to geology, source, ventilation and construction qualities of each building.

Because radon gas is a known risk, people around the world are taking action to test for the gas and prevent exposure to it. Because radon gas is odorless, colorless, tasteless and inert, the only way to detect its presence is by performing a radon test using a radon measurement device. Screening is the only way to reduce radon risk and there is a need for improved screening methods.

The subject matter claimed herein is not limited to embodiments that solve any disadvantages or that operate only in environments such as those described above. Rather, this background is only provided to illustrate one example technology area where some embodiments described herein may be practiced.

SUMMARY OF SOME EXAMPLE EMBODIMENTS

An aspect of an embodiment includes a radon measurement device that includes a housing, a diffusion chamber, a diffusion chamber sensor, a diffusion pathway, a clock circuit, measurement circuitry, and a triggering mechanism. The diffusion chamber is disposed in an internal cavity of the housing. The housing includes a vent. The diffusion chamber sensor detects radioactive decay of radon and generates an electrical signal. The diffusion pathway enables introduction of ambient air into the diffusion chamber. The clock circuit outputs time data. The measurement circuitry receives the electrical signal and associates therewith a particular time datum. The triggering mechanism selectively isolates the vent from an environment and selectively triggers the measurement circuitry. Responsive to a triggering action on the triggering mechanism, the diffusion pathway is fluidly connected with the environment and functionality of the measurement circuitry is initiated. The detection data set is limited to a period between the triggering action and a particular measurement interval.

Another aspect of an embodiment may include a method of radon detection. The method of radon detection may be performed by a single use, single calibration device. The method may include, responsive to a triggering action imposed on the triggering mechanism, fluidly connecting a diffusion pathway with the ambient environment via a vent that is defined in a housing. The diffusion pathway may enable introduction of ambient air into a diffusion chamber coupled to the diffusion pathway and the vent. The connecting the diffusion pathway with the ambient environment via the vent may include moving a vent cover relative to the vent to selectively isolate the diffusion pathway from the ambient environment. Additionally, responsive to the triggering action, the method may include initiating functionality of a measurement circuitry. The fluidly connecting and the initiating functionality may occur concurrently or substantially concurrently. The initiating functionality of a measurement circuitry may include removing an electrical insulator that prior to the triggering action may be positioned between the power source and the measurement circuitry or changing a state of an electrical switch that selectively electrically isolates the measurement circuitry from the power source. In detail, the vent cover may define a vent opening and a protrusion positioned relative to the electrical switch. The triggering action may include movement of the vent cover such that the vent opening may be aligned or substantially aligned with the vent, and concurrently actuation of the electrical switch by a protrusion to electrically couple the power source with the measurement circuitry. Additionally or alternatively, prior to the triggering action, the vent cover may be positioned over the vent such that the diffusion pathway is isolated from the ambient environment. The vent cover may be integrally formed with or otherwise coupled to the electrical insulator. The triggering action may include removal of the vent cover along with a second feature. The method may include, responsive to receipt of the triggering action, changing a state of a functional indicator from a first state to a second state. The method may include detecting, by a diffusion chamber sensor positioned in the diffusion chamber within the housing, radioactive decay of radon in the ambient air. The diffusion chamber sensor may include a photodiode, an amplifier, and a faraday chamber that protects the amplifier and the photodiode from electrostatic interference. The diffusion chamber may be disposed in the housing and may include a casing that substantially prevents introduction of ambient light into the diffusion chamber. The method may include outputting time data, which may occur responsive to an initiation signal. The method may include generating an electrical signal responsive to detection of the radioactive decay. The method may include receiving at the measurement circuitry the electrical signal indicative of the radioactive decay from the diffusion chamber sensor. The method may include associating with the electrical signal a particular time datum at which the electrical signal is received in a detection data set. The method may include limiting the detection data set to a time period between the triggering action and a particular measurement interval, which may be about forty-eight hours. Upon expiration of the time period, the method may include storing the detection data set on a non-transitory storage medium positioned in the housing and communicatively coupled to the measurement circuitry. Responsive to expiration of the particular measurement interval, the method may include changing the state of the functional indicator from the second state to a third state. The method may include enabling access to the detection data set stored on the medium via an information output. The information output may include a removable non-transitory medium interface device or a wireless transmitter. The method may include detecting a physical movement of the device relative to an initial placement location. The method may include communicating tamper data indicative of the physical movement to measurement circuitry. The method may include associating a timestamp at which the physical movement occurs with the tamper data and incorporating the tamper data and the timestamp associated therewith into the detection data set. The method may include continuing detection of radioactive decay of radon in the ambient air following the expiration of the particular measurement interval. The method may include generating a subsequent detection data set based on the continued detection. The subsequent detection data set may be stored. The method may include changing the state of the functional indicator to one or more subsequent states at the expiration of each of the subsequent measurement intervals. The subsequent measurement intervals may include a first subsequent measurement interval that is seventy-two hours following the triggering action, a second subsequent measurement interval that is seven days following the triggering action, a third subsequent measurement interval that is 30 days following the triggering action, a fourth subsequent measurement interval that is 90 days following the triggering action, and a fifth subsequent measurement interval that is 1 year following the triggering action.

The object and advantages of the embodiments will be realized and achieved at least by the elements, features, and combinations particularly pointed out in the claims. It is to be understood that both the foregoing general description and the following detailed description are exemplary and explanatory and are not restrictive of the present disclosure, as claimed.

BRIEF DESCRIPTION OF THE DRAWINGS

Example embodiments will be described and explained with additional specificity and detail through the use of the accompanying drawings in which.

DESCRIPTION OF SOME EXAMPLE EMBODIMENTS

Figure 1:
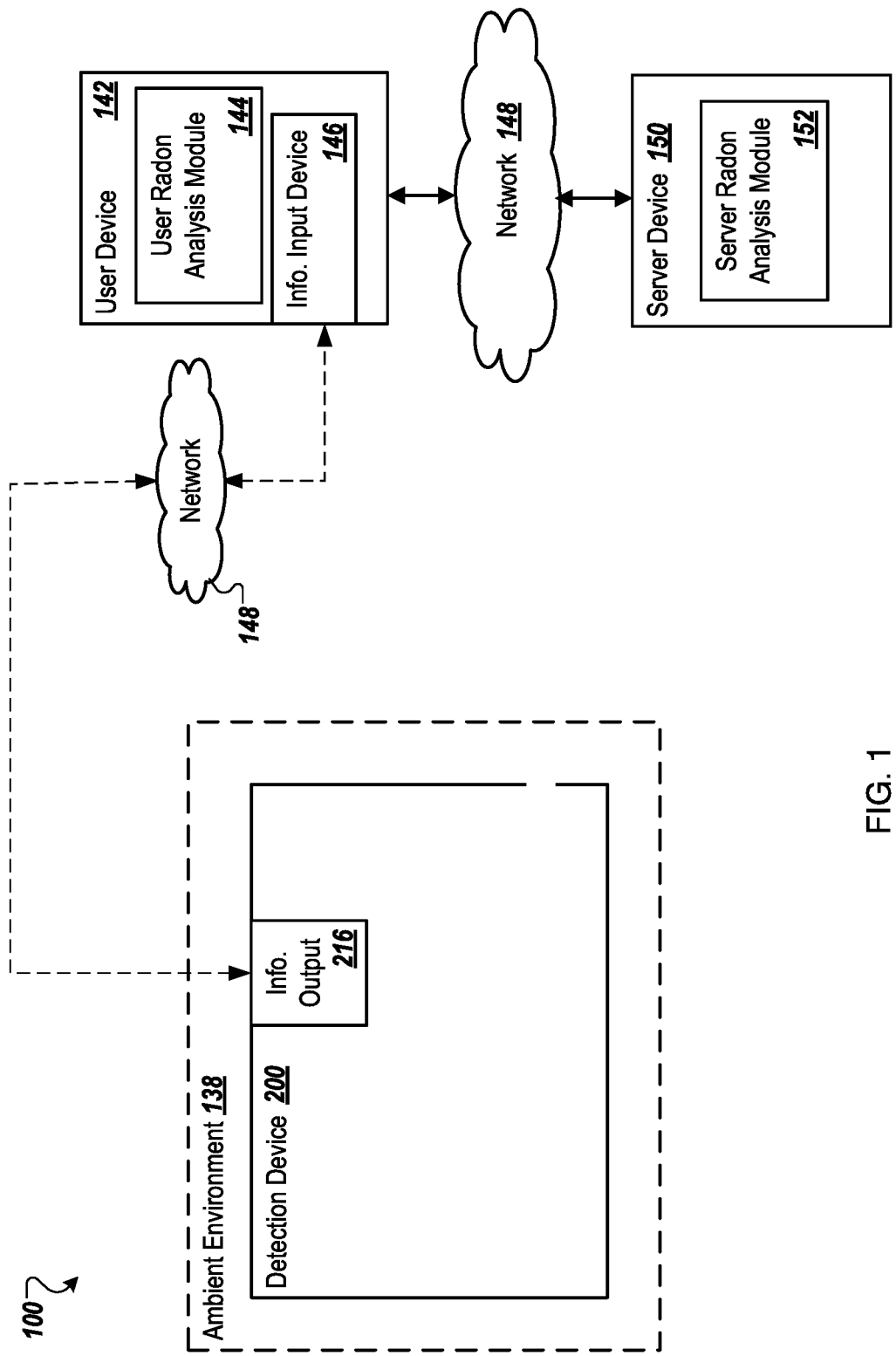
FIG. 1 illustrates an example analysis environment in which a single use, single calibration device may be implemented.

Current technologies offer radon measurements at varying cost, informational, and duration levels. However, current technologies are problematic and can provide end-users with inaccurate data causing them to either be exposed to more radon than reported, which may increase their lung cancer risk or impact a user's investment decision on expensive radon abatement equipment.

For example, traditionally, radon measurements are performed either by professional providers or by end users. Professional radon measurement providers usually belong to a certification organization or government licensing program. Professionals are hired by end users to provide radon gas measurements in structures such as homes, schools, government buildings, and commercial buildings. Professional radon measurement providers are usually for-profit providers. The professional measurements require a professional provider to travel to the site, deploy a measurement device, and return after forty-eight hours to retrieve the measurement device. After the measurement device is retrieved, data indicative of radon levels may be accessed and a report may be generated based on the accessed data. The report generated based on the professional measurement devices may show hourly radon levels. From the hourly radon levels, an average radon concentration may be calculated. An owner of the structure may base an abatement system on the average radon concentration.

The value in having a graphical report is to show how radon entry may vary in the building. This can help determine test validity, tampering, weather impact and other factors that can help determine if further testing or mitigation is required. Many radon tests that are provided by professionals are done using electronic radon measurement equipment. These professional-caliber, electronic measurement devices are reset and then reused by the professional multiple times on multiple properties.

Over time, these units can come out of calibration, rendering inaccurate results. The professional association of the American Association of Radon Scientists and Professionals (AARST) certifies professionals and laboratories for performing radon measurements. AARST has set forth device protocols and quality assurance/quality control programs that mandate annual re-calibration of electronic radon measurement devices. To ensure accuracy of the testing equipment, certified radon measurement providers must have their equipment calibrated on an annual basis. This annual calibration is a commercially viable solution; however, the annual calibration does not prevent equipment from prematurely coming out of calibration. Moreover, because these electronic radon measurement devices have expensive upfront costs, provider costs associated with delivery, retrieval, reporting and QA/QC; they are not the most economical solution to consumer demand for radon measurements.

An economical solution to the problem of cost in professional measurement devices, calibration, and deployment is the passive radon test device. In the passive radon test devices, activated charcoal and/or liquid scintillation are most commonly used. The passive radon test devices are short-term, passive radon measurement devices.

The charcoal test kits are a single use measurement device that can be used by non-professionals and professionals. The duration of the test ranges from a minimum of about forty-eight hours up to about seven days. The end user or professional follows the instructions that include the national standards for placing the measurement devices. After the charcoal has been exposed for the duration specified in the instructions, the test is completed by sealing the charcoal to stop exposure.

The end user or the professional completes the vital information card by writing down the exact time the charcoal was exposed and writing the exact time it was sealed. They then package the sample and ship it to the lab for analysis. The shipping transit can be long before it reaches the lab depending on location. Once the lab receives the kit, the lab measures the radon decay products in the sample and calculates the quantities vs the time the sample was exposed to determine the radon concentration.

The lab provides the end-user with a single number which is the Average Radon Level. The single number is provided because the charcoal does not allow hourly readings with these passive devices. Thus, the results include a margin of error estimated by factors that can be derived from shipping time, over-exposure, vapor content or other factors that can affect radon absorption and/or measurement.

The benefit is that charcoal test kits can be manufactured inexpensively and are simple to deploy for non-professional users. The charcoal test is an economical solution for the consumer and a good method for initial sampling. The problems with the current charcoal technology include, user error in completing vital timestamp data, loss in shipping transit, over exposure due to forgetting about the sample, damaged package in shipping, time sensitivity, humidity, and environmental effects on the charcoal and expiration dates.

Another commonly used, short-term passive measurement method is called liquid scintillation. The deployment, user process, data point and drawbacks are similar to activated charcoal. The process to use a charcoal or Liquid Scintillation test kit and receive your results can take more than twice the time as electronic radon measurements. Thus, the end user may have to wait a considerable time before knowing a potential health risk associated with Radon.

Yet another passive method for radon measurement is the alpha track radon test kit. This test kit is economically similar to the activated charcoal tests in cost and processes. However, again the consumer must accurately complete the vital information and place it in a specified location according to the instructions and radon measurement standards. Alpha track kits can be placed for a duration range from about five to about ten days on the short-term and long-term range of about 90 days to about a year.

The alpha track radon test kits work by counting the alpha radiation impressions on a plastic sample. The alpha track radon test kits also require lab analysis. Similar problems can occur from user error, shipping, and damage factors before arriving at the lab. The alpha track radon test kits differ from charcoal and liquid scintillation in that they are not susceptible to humidity and temperature influence. They also can provide longer term measurements that will give a consumer a better idea of exposure to the varying levels of radon entered over time. However, problems exist with these radon measurement devices that include, improper timestamp information by user, loss or damage in shipping and over exposure from forgetting about the sample.

Lastly, there are radon measurement devices that are designed for continuous radon monitoring. These devices are geared to the non-professional market. These devices provide a digital reading of the radon gas levels that is interpreted visually and not by a report. These devices can show end-user fluctuations in radon levels over time and can sound an audible alarm if radon levels increase above the EPA action level. The American Association of Radon Scientists and Technologists have not certified these devices because QA/QC standards cannot be controlled on these devices. An electronic radon measurement device must be re-calibrated to make sure they are providing accurate readings. The current technology for these radon measurement monitors are cost prohibitive for consumers who are looking for the initial short-term sample.

Some example devices involved in Radon measurement are described in U.S. Pat. Nos. 5,489,780; 8,143,584; 4,992,658; and 9,354,214, which are incorporated herein by reference in their entireties.

Accordingly, some embodiments described in the present disclosure provide end users with an economical solution to current technology problems. These embodiments provide a solution to cost, calibration, user error, and shipping problems that exist with existing technologies. For example, some embodiments create a means to provide radon gas measurements that are in calibration, have multiple data points, are self-timed, and simple for radon professionals and non-professionals alike.

Some example embodiments are described with reference to the accompanying drawings. In the accompanying drawings, features with like item numbers indicate like function and structure unless described otherwise.

FIG. 1 illustrates an example analysis environment 100 in which radon detection and measurement may be implemented according to at least one embodiment described in the present disclosure. In the analysis environment 100, a detection device (device) 200 may be implemented in an ambient environment 138. The device 200 may be deployed in the ambient environment 138 to detect and to measure radon gas in the ambient environment 138. For example, ambient air in the ambient environment 138 may enter the device 200. The radon in the ambient air may be detected and measured. A detection data set that includes a time series of the measured radon may be stored at the device 200.

To enable access to the detection data set, the device 200 may include an information output 216 (in FIG. 1, "info. output 216"). The information output 216 may be configured to access or otherwise enable transfer of the detection data set from the device 200. The information output 216 may include one or more pieces of hardware configured to receive and send communications that include the detection data set. The information output 216 may include one or more of an antenna, a wired port, and modulation/demodulation hardware, among other communication hardware devices. In some embodiments, the information output 216 may be configured to present the communication to a processor or processing device of the device 200 or to send a communication from the processor to a user device 142 and/or a server device 150 via one or more networks 148.

In the analysis environment 100, the server device 150 and the user device 142 may include any hardware-based computing system that includes a processor and non-transitory storage medium. The server device 150 and the user device 142 may be configured for network communication in the analysis environment 100 via the network 148. Some examples of the user device 142 may include a personal computer, a laptop computer, a table computer, a smart phone, and the like. The server device 150 may include one or more hardware server devices or other computing devices configured for communication via the network 148.

The server device 150 may include a server radon analysis module 152. The user device 142 may include a user radon analysis module 144. The server radon analysis module 152 and/or the user radon analysis module 144 (collectively, analysis modules 152/144) may be configured to receive the detection data set and to process it. For example, the analysis modules 152/144 may be configured to interpret the detection data set such that it may be read and/or displayed. In addition, the analysis modules 152/144 may derive one or more values from the detection data set. Accordingly, a user may have access to the detection data set and information included therein in real time or without material delay.

The analysis modules 152/144 and one or more components or modules thereof described throughout the present disclosure may be implemented using hardware including a processor, a microprocessor (e.g., to perform or control performance of one or more operations), a field-programmable gate array (FPGA), or an application-specific integrated circuit (ASIC). In some other instances, the analysis modules 152/144 and one or more components or modules thereof may be implemented using a combination of hardware and software. Implementation in software may include rapid activation and deactivation of one or more transistors or transistor elements such as may be included in hardware of a computing system. Additionally, software defined instructions may operate on information within transistor elements. Implementation of software instructions may at least temporarily reconfigure electronic pathways and transform computing hardware.

For example, in some embodiments, the information output 216 may include a device port such as a universal serial port (USB) port or another suitable port. A user may position a USB memory device in the information output 216. The detection data set may be transferred to the USB memory device. The user may then introduce the USB memory device to an information input device 146 of a user device 142.

The user radon analysis module 144 may be configured to process the detection data set. For instance, the user radon analysis module 144 may be configured to display some portion of the detection data set, derive one or more values (e.g., average radon exposure) from the detection data set, etc. Additionally or alternatively, the user radon analysis module 144 may be configured to access the server radon analysis module 152 on the server device 150 via the network 148. The server radon analysis module 152 may supplement processing provided by the user radon analysis module 144 or may process the detection data set.

In some embodiments, the information output 216 may include a BLUETOOTH® transmitter. In these embodiments, instead of positioning a USB memory device in the information output 216, a user may sync or pair the user device 142 with the device 200. The detection data set may be transferred to the user device 142 using the BLUETOOTH communication protocol. The analysis modules 152/144 may be configured to process the detection data set as described above.

In the analysis environment 100, the network 148 may include any network configured for communication of signals between the device 200, the user device 142 and the server device 150. For instance, the network 148 may include a local area network (LAN), a wide area network (WAN) (e.g., the Internet), and/or other interconnected data paths across which multiple devices may communicate. In some embodiments, the network 148 may include a peer-to-peer network. The network 148 may also be coupled to or include portions of a telecommunications network that may enable communication of data in a variety of different communication protocols. In some embodiments, the network 148 includes or is configured to include a BLUETOOTH® communication network, a Wi-Fi communication network, a ZigBee communication network, an extensible messaging and presence protocol (XMPP) communication network, a cellular communications network, any similar communication networks, or any combination thereof for sending and receiving data. The data communicated in the network 148 may include data communicated via short messaging service (SMS), multimedia messaging service (MMS), hypertext transfer protocol (HTTP), direct data connection, wireless application protocol (WAP), e-mail, or any other protocol that may be implemented in the analysis environment 100.

Modifications, additions, or omissions may be made to the analysis environment 100 without departing from the scope of the present disclosure. For example, the analysis environment 100 may include one or more devices 200, one or more user devices 142, one or more server devices 150 or any combination thereof. Moreover, the separation of various components and servers in the embodiments described herein is not meant to indicate that the separation occurs in all embodiments. Moreover, it may be understood with the benefit of this disclosure that the described components and servers may generally be integrated together in a single component or server or separated into multiple components or servers.

Figure 2A:
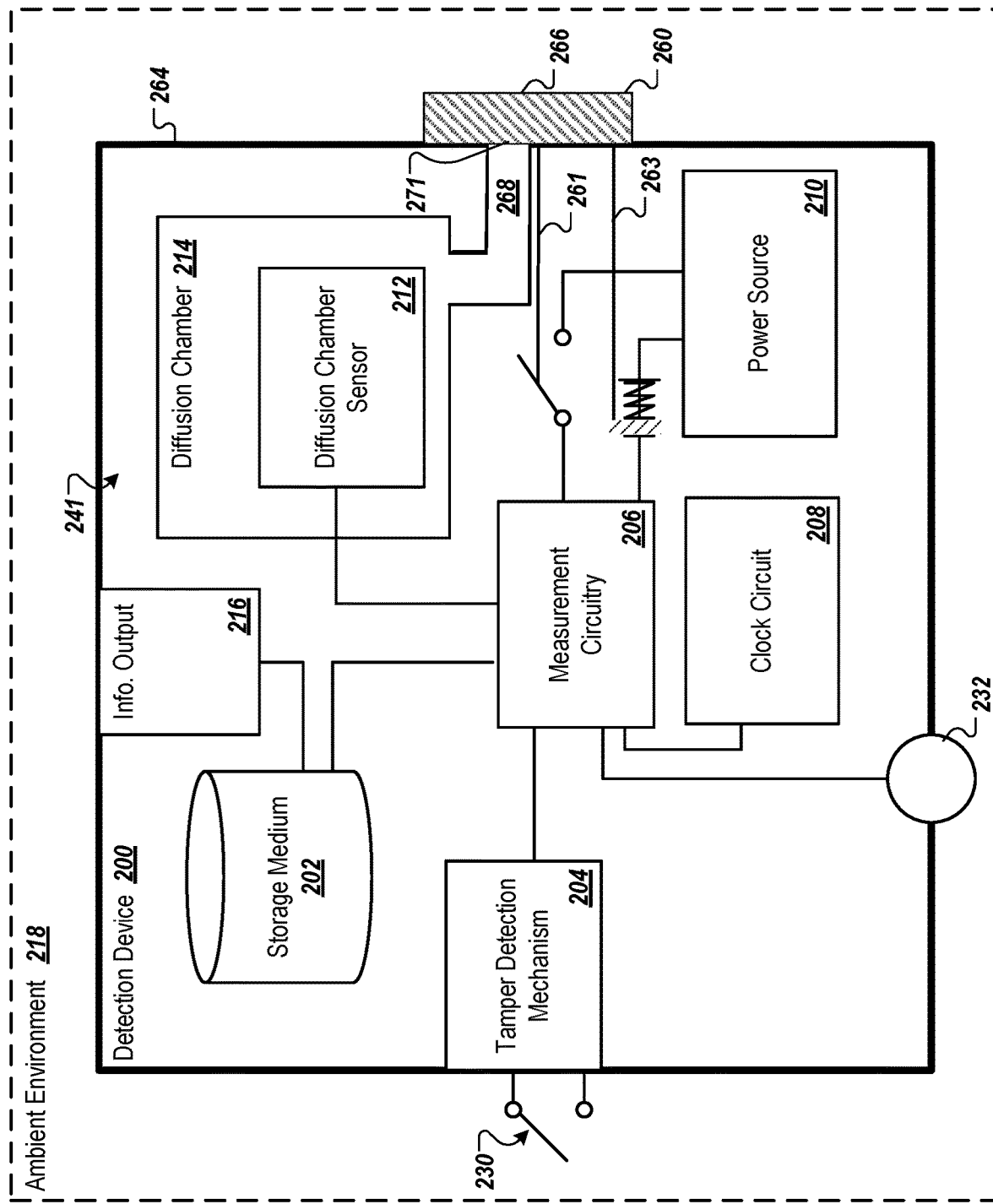
FIG. 2A illustrates an example embodiment of the device in a pre-deployed configuration.
Figure 2B:
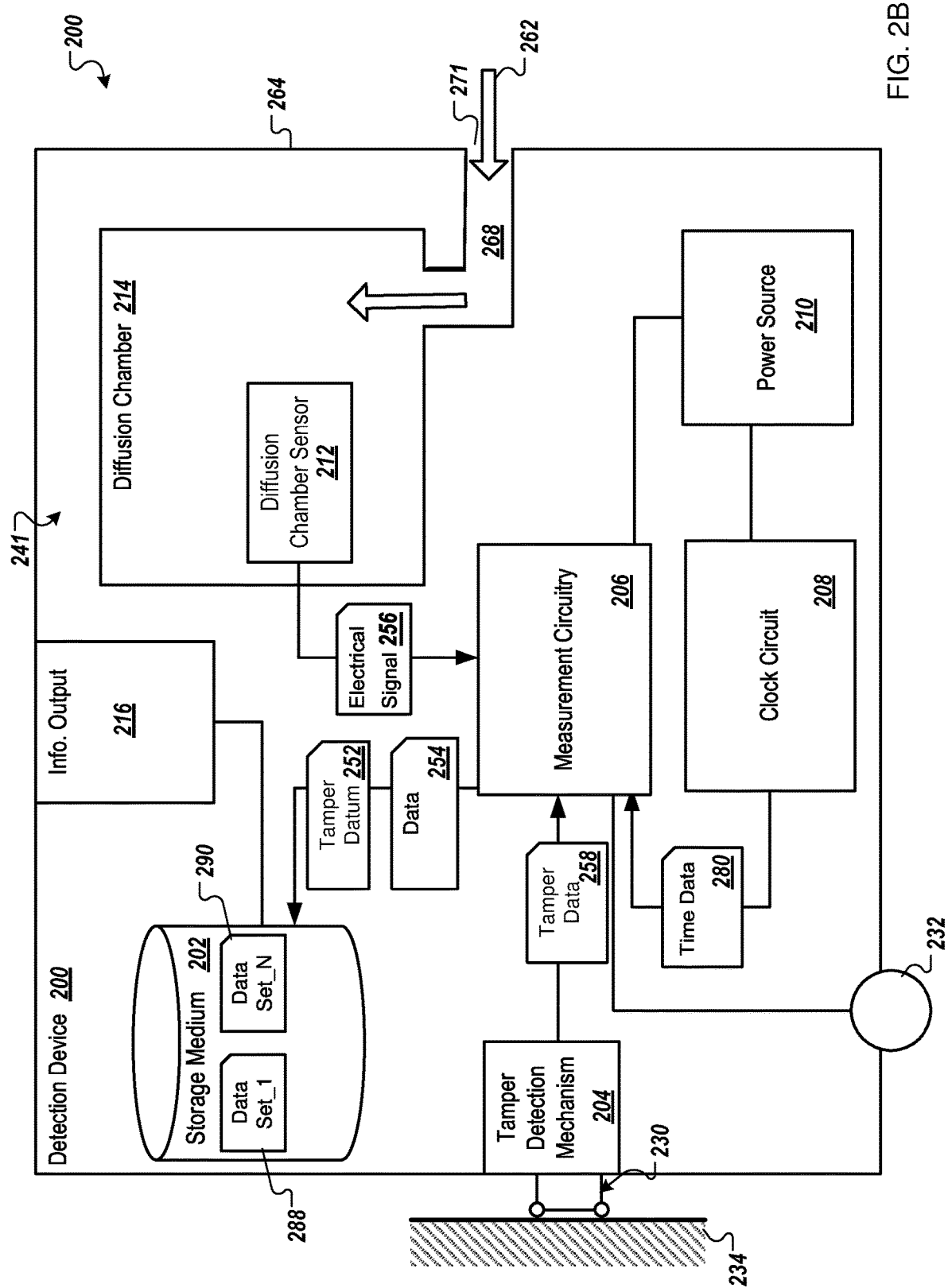
FIG. 2B illustrates an example embodiment of the device in a deployed configuration.

FIGS. 2A and 2B illustrate an example embodiment of the device 200 of FIG. 1. FIG. 2A depicts the device 200 in a pre-deployed configuration, which is before a triggering action as described below. FIG. 2B depicts the device 200 in a deployed configuration. In FIGS. 2A and 2B, the device 200 may be placed in an ambient environment 218, which may correspond to the ambient environment 138 of FIG. 1. The ambient environment 218 may include an atmospheric or air-containing environment of a structure such as a house or building. For example, the ambient environment 218 may include a basement of a residence. The ambient environment 218 may have ambient air 262 (FIG. 2B), which may include radon gas. The device 200 may be implemented in the ambient environment 218 to detect and to measure an amount of radon gas in the ambient air 262. Based on the measurement of the radon gas, an end user such as an owner or manager of the structure may abate or mitigate the radon gas.

The device 200 may be configured for a single use and for a single calibrated measurement interval. Additionally, the device 200 may be configured to reduce or eliminate user error and to impart regularity and reliability in detection data sets generated by the device 200. For example, the device 200 may include a triggering mechanism 266 (FIG. 1). The triggering mechanism 266 may enable a concurrent or substantially concurrent connection between a diffusion pathway 268 and the ambient environment 218 along with initiation of functionality of a measurement circuitry 206. As used in the present disclosure, concurrent or substantially concurrent may include simultaneous, immediately following or without material delay, such as a fraction of a second (e.g., 0.5 seconds or less). Hereinafter in the present disclosure, "concurrently or substantially concurrently" is referred to as "concurrently."

Thus, to deploy the device 200, a user may impose a triggering action on the triggering mechanism 266. The triggering action may enable the ambient air 262 to enter the device 200. Concurrently, the functionality of measurement circuitry 206 may be initiation, which may begin the detection and measurement of radon gas in the ambient air 262. The measurement circuitry 206 may be configured to generate a detection data set that is indicative of the radon gas measured in the ambient air 262. Because the functionality of the measurement circuitry 206 occurs concurrently with the connection, one or more initial data points and a measurement interval may be reliable. That is, the detection data set may not include any readings of radon or a lack thereof prior to a connection between the diffusion pathway 268 and the ambient environment 218. For instance, if the connection occurs prior to initiation of the functionality of the measurement circuitry 206, then the ambient air 262 may be present in the diffusion pathway 268 and/or a diffusion chamber 214 before the measurement circuitry 206 is ready to detect radon gas. Alternatively, if the measurement circuitry 206 is functional but the diffusion pathway 268 is isolated from the ambient environment 218, the measurement circuitry 206 may read a period of little or no radon gas because the ambient air 262 is not present in the diffusion pathway 268 and/or the diffusion chamber 214. Often, the measurement of radon gas is performed for a particular measurement interval. After the measurement, an average radon gas level may be calculated, which may be used to recommend or size an abatement system. The presence of erroneous data at the initial stages of the measurement interval may skew the radon gas levels in the detection data set, which may alter the average. In some circumstances, inaccurate detection data sets may result in an end user deciding not to install an abatement system when one is beneficial or to install an abatement system when one is unnecessary.

In addition, for accurate radon measurement, the device 200 should be placed in a single location for the particular measurement interval and for subsequent measurement intervals. Movement of the device 200 undermines the accuracy of the measurements and detection data set based thereon. For instance, if half of the measurements are conducted near a window and the other half are conducted far from the window, then the temperature changes, atmospheric conditions, etc., may be improperly reflected in the detection data set.

Accordingly, in some embodiments, the device 200 may include a tamper detection mechanism 204. The tamper detection mechanism 204 may be configured to detect when the device 200 is physically moved from an initial position in the ambient environment 218. For instance, in the embodiment of FIGS. 2A and 2B, the tamper detection mechanism 204 may include a switch 230. In the pre-deployed configuration of FIG. 2A, the switch 230 may be in a first state (in FIG. 2A, the switch 230 is open, but this is not meant to be limiting). When the device 200 is initially placed in the ambient environment 218 (e.g., prior to the triggering action) as depicted in FIG. 2B, the switch 230 may change to a second state (in FIG. 2B, the switch 230 is closed, but again this is not meant to be limiting). The position of the switch 230 may be maintained in the second state by a feature or element of the structure, which is represented in FIG. 2B by a wall 234. The triggering action may be imposed on the triggering mechanism 266, which may begin detection and measurement of radon gas in the ambient air 262. Movement of the device 200 relative to the wall 234 may cease maintenance of the switch 230 in the second state. Responsive to such movement, the tamper detection mechanism 204 may generate tamper data 258. The tamper data 258 may be reflected in the detection data set. Accordingly, the detection data set may record whether and when the device 200 has been moved following positioning the device 200 in an initial position. Knowledge of the movement of the device 200 may indicate which portions of the detection data set, if any, may have compromised data due to a change in position.

In addition, a source of errors in radon detection is the lack of or expiration of calibration of radon detection and measurement devices. For instance, in professional radon mitigation, calibration is required each year to maintain a license. Also, some end user devices cannot be calibrated. Accordingly, the device 200 in the pre-deployed configuration is calibrated and sealed. Thus, prior to deployment, the device 200 is in a calibrated state. Accordingly, the data read by the device 200 may properly detect and measure radon in the ambient environment 138. Additionally, in some embodiments, the device 200 may be configured with an upper limit respective to the time during which radon is measured. The device 200 may include an upper limit that is less than or equal to a year. Accordingly, the upper limit may prevent the device 200 from being used when the calibration is expired.

With reference to FIGS. 2A and 2B, in addition to the triggering mechanism 266, the diffusion pathway 268, the diffusion chamber 214, the measurement circuitry 206, the tamper detection mechanism 204, and the switch 230, the device 200 may include components such as a housing 264, a diffusion chamber sensor 212, a diffusion pathway 268, a clock circuit 208, a non-transitory storage medium 202, an information output 216, a power source 210, and a functional indicator 232. The triggering mechanism 266, the diffusion pathway 268, the diffusion chamber 214, the measurement circuitry 206, the tamper detection mechanism 204, the switch 230, the housing 264, the diffusion chamber sensor 212, the diffusion pathway 268, the clock circuit 208, the non-transitory storage medium 202, the information output 216, the power source 210, and the functional indicator 232 are collectively referred to as device components. Each of the device components are described in the following paragraphs.

The housing 264 may define an internal cavity 241. In general, the remaining device components are positioned in the internal cavity 241. Thus, the device 200 may include an enclosed structure, which may be formed by the housing 264. The housing 264 may be comprised of a plastic, a metal, or another suitable material.

The housing may include a vent 271. The vent 271 is an opening in the housing 264 formed at the end of the diffusion pathway 268. In the embodiment of FIGS. 2A and 2B there is a single vent 271. In other embodiments, there may be two or more vents 271.

The diffusion chamber 214 may be disposed in the internal cavity 241. The diffusion chamber may include a casing that substantially prevents introduction of ambient light into the diffusion chamber 214. Within the diffusion chamber 214 may be the diffusion chamber sensor 212. The diffusion chamber sensor 212 may be configured to detect radioactive decay of radon in the diffusion chamber 214. Responsive to the detection of the radioactive decay, the diffusion chamber sensor 212 may be configured to generate an electrical signal 256 that is representative of detected radon. The electrical signal 256 may be communicated to the measurement circuitry 206.

In some embodiments, the diffusion chamber sensor 212 may include a photodiode, an amplifier, and a faraday chamber that protects the amplifier and the photodiode from electrostatic interference. In other embodiments, the diffusion chamber sensor 212 may include another sensor capable of detecting radon in the ambient air 262.

The diffusion pathway 268 is coupled between the diffusion chamber 214 and the vent 271. For instance, the vent 271 may be at an end of the diffusion chamber 214. The diffusion pathway 268 may enable introduction of ambient air 262 into the diffusion chamber 214. In some embodiments and some circumstances, some of the radioactive decay may occur in the diffusion pathway 268.

The clock circuit 208 may be configured to generate a clock signal, time data, or a synchronization signal (time data 280). The time data 280 includes a global time (e.g., a current time) and/or an on-going clock signal that begins with the triggering action. In some embodiments, the clock circuit 208 may output the time data 280 responsive to an initiation signal. The initiation signal may be communicated by the measurement circuitry 206 in response to the triggering action.

The measurement circuitry 206 may be communicatively coupled to the diffusion chamber sensor 212 and the clock circuit 208. The measurement circuitry 206 may be configured to receive the electrical signal 256 indicative of the radioactive decay from the diffusion chamber sensor 212 and to associate with the electrical signal 256 a particular time datum at which the electrical signal is received in a detection data set 288 or 290. The particular time datum may be based on the time data 280 received from the clock circuit 208.

The triggering mechanism 266 (FIG. 2A) may include a first feature 260 that selectively physically isolates the vent 271 from the ambient environment 218. The triggering mechanism 266 may also include a second feature 261 or 263 that selectively electrically triggers the measurement circuitry 206. The triggering mechanism 266 may be configured such that responsive to the triggering action imposed on the triggering mechanism 266, the first feature and the second feature are concurrently affected such that the diffusion pathway 268 is fluidly connected with the ambient environment 218 via the vent 271 and functionality of the measurement circuitry 206 is initiated.

For example, the first feature 260 may include a vent cover that moves relative to the vent to selectively isolate the diffusion pathway 268 from the ambient environment 218. In these and other embodiments, the second feature may include an electrical insulator that prior to the triggering action (in FIG. 2A) is positioned between the power source 210 and the measurement circuitry 206 or an electrical switch that selectively electrically isolates the measurement circuitry 206 from the power source 210. Some additional details of some example triggering mechanisms 266 are provided with reference to FIGS. 5A-6B.

In some embodiments, the measurement circuitry 206 may be configured to limit the detection data set 288 and 290 to a time period between the triggering action and a particular measurement interval. The For example, the particular measurement interval may include forty-eight hours following the triggering action.

The non-transitory storage medium 202 may be positioned in the housing 264 and communicatively coupled to the measurement circuitry 206. The measurement circuitry 206 may be configured to communicate data 254 representative of the electrical signal 256 to the storage medium 202. The data 254 may be stored in detection data sets 288 and 290. Some additional details of some example data sets are provided with reference to FIG. 3. The detection data sets 288 and 290 may be batch transferred to the storage medium 202 upon expiration of the time period. The detection data sets 288 and 290 may be stored on the storage medium 202 until accessed via the information output 216 as described above.

The functional indicator 232 may be configured to change from a first state to a second state responsive to the triggering action. For example, the first state may be an off or de-energized state, and the second state may be a blinking amber light at a first rate. Additionally, the functional indicator 232 may change from the second state to a third state responsive to expiration of the particular measurement interval and/or subsequent measurement intervals. The state of the functional indicator 232 may indicate to a user that detection data sets 288 and/or 290 are available for download via the information output 216. In some embodiments, the functional indicator 232 may include a light emitting diode (LED), a light, a vibrator, an audible alarm, or another suitable device or system that may indicate an expiration of a measurement interval.

In some embodiments, the measurement circuitry 206 is further configured to continuing detection of radioactive decay of radon in the ambient air 262 following the expiration of a first particular measurement interval. In particular, the measurement circuitry 206 may be configured to continue detection for one or more subsequent measurement intervals. Based on the detected radon in the subsequent measurement intervals, the measurement circuitry 206 may generate one or more subsequent detection data sets (e.g., 288 or 290). Each of the one or more subsequent detection data sets may span one of the subsequent measurement intervals.

In some embodiments, the subsequent measurement intervals include a first subsequent measurement interval that is seventy-two hours following the triggering action, a second subsequent measurement interval that is seven days following the triggering action, a third subsequent measurement interval that is 30 days following the triggering action, a fourth subsequent measurement interval that is 90 days following the triggering action; a fifth subsequent measurement interval that is one year following the triggering action, or some combination thereof. In these and other embodiments, the fifth subsequent measurement interval may limit or stop detection. As mentioned above, calibration of the device 200 may end at one year. Thus, the measurement circuitry 206 may prevent further detection. Upon the expiration of one or more or each of the subsequent measurement intervals, the functional indicator 232 may be configured to change state.

The tamper detection mechanism 204 may be configured to detect a physical movement of the device 200 relative to an initial placement location. As described above, the tamper detection mechanism 204 may include the switch 230 which may be actuated by moving the switch relative to the wall 234. In other embodiments, the tamper detection mechanism 204 may include a gyroscopic sensor, an accelerometer, a photodiode, combinations thereof, or another suitable device or system.

The tamper detection mechanism 204 may communicate tamper data 258 indicative of the physical movement to measurement circuitry 206. The measurement circuitry 206 may be configured to associate a timestamp at which the physical movement occurs with the tamper data 258. The timestamp may be based on the time data 280. The measurement circuitry 206 may be configured to communicate a tamper datum 252 to the storage medium 202. The tamper datum 252 may include the timestamp at which the physical movement occurs. The tamper datum 252 may be indicated in the detection data set 288 or 290 to which it pertains.

Modifications, additions, or omissions may be made to the device 200 without departing from the scope of the present disclosure. For example, the device 200 may include one or more or any or any combination of the device components. Moreover, the separation of various device components in the embodiments described herein is not meant to indicate that the separation occurs in all embodiments. Moreover, it may be understood with the benefit of this disclosure that the described device components may generally be integrated together in a single component or separated into multiple components or servers.

Figure 3A:
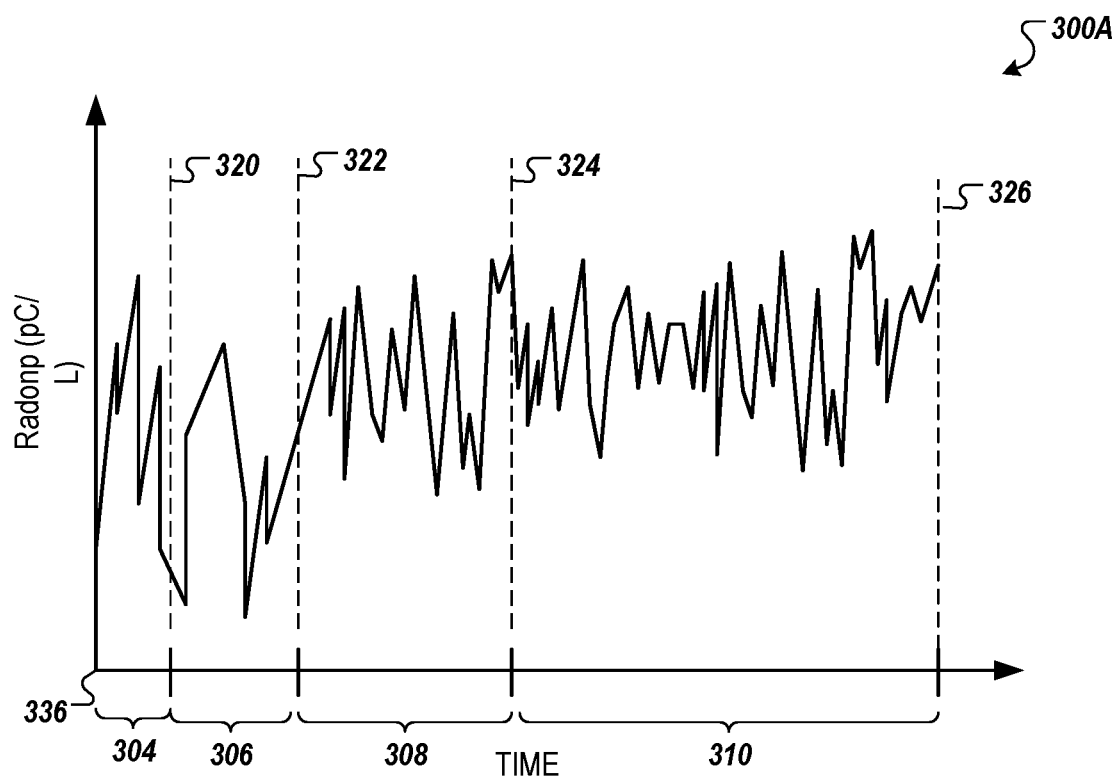
FIG. 3A is a first example detection data set that may be generated by the device of FIGS. 1-2B.
Figure 3B:
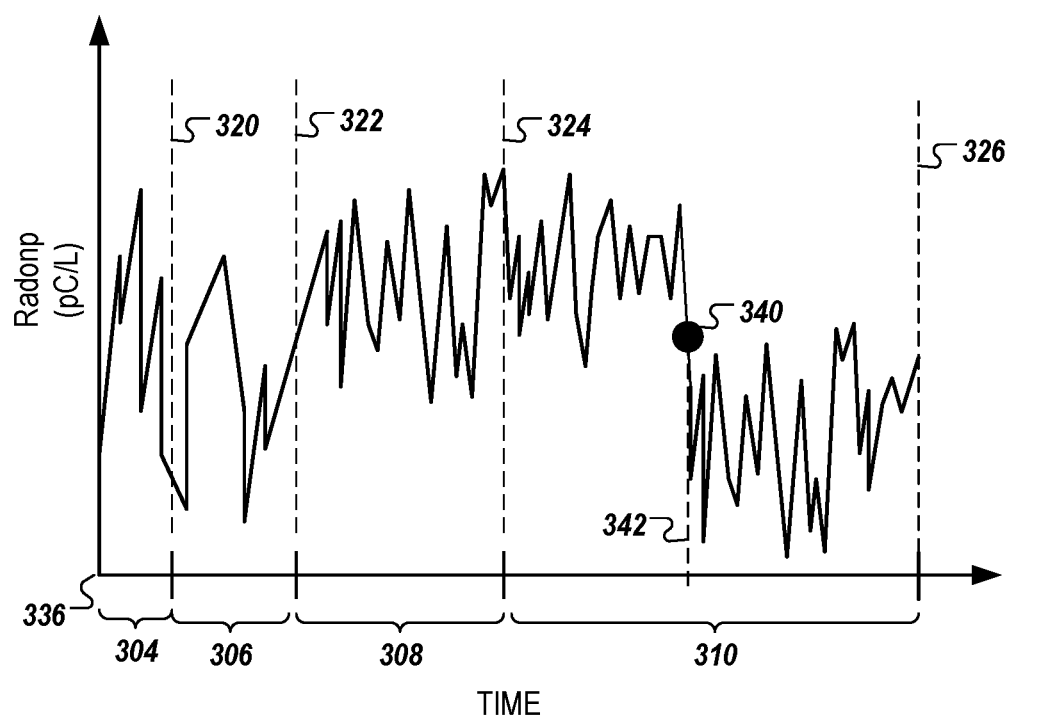
FIG. 3B is a second example detection data set that may be generated by the device of FIGS. 1-2B.

FIGS. 3A and 3B depict example detection data sets 300A and 300B that may be generated by the device 200 of FIGS. 1-2B. For example, FIG. 3A is a first example detection data set 300A that may be generated by the device 200 of FIGS. 1-2B. FIG. 3B is a second example detection data set 300B that may be generated by the device 200 of FIGS. 1-2B.

In the detection data sets 300A and 300B, the radon detected may be plotted on the y-axes. In some embodiments, units of the y axes may be in picocuries per liter (pC/L). The time may be plotted on the x-axes and may begin at an initial time 336 that corresponds to a triggering action. In some embodiments, the time may have the units of seconds, minutes, or hours. In the data sets 300A and 300B multiple measurement intervals 304, 306, 308, 310 are included. The first measurement interval 304 may include the particular measurement interval. The measurement intervals 306, 308, and 310 may be subsequent measurement intervals.

A first measurement interval 304 may end at a first time 320. Measurement circuitry such as the measurement circuitry 206 of FIGS. 2A-2B may be configured to batch download radon data of the first measurement interval 304 to a storage medium such as the storage medium 202. The measurement circuitry may continue to detect and measure radon. Additionally, a functional indicator such as the functional indicator 232 of FIGS. 2A and 2B may change state at the first time 320, which may indicate to a user that the radon data of the first measurement interval 304 is available and/or accessible. Similarly, at each of a second measurement interval 306, a third measurement interval 308, and a fourth measurement interval 310, the measurement circuitry may be configured to batch download radon data to the storage medium. Additionally, the functional indicator may change state at a second time 322, a third time 324, and a fourth time 326 at which the second measurement interval 306, the third measurement interval 308, and a fourth measurement interval 310 ends.

In some embodiments, the measurement intervals 304, 306, 308, and 310 may include seventy-two hours following the initial time 336, seven days following the initial time 336, 30 days following the initial time 336, 90 days following the initial time 336, and one year following the initial time 336.

In the second data set 300B, the data included in the fourth measurement interval 310 includes a tamper datum 340. The tamper datum 340 may reflect a tamper data that is generated responsive to movement of the device 200. A timestamp 342 of the tamper datum 340 is included in the second detection data set 300B. Inclusion of the tamper datum 340 indicates that the radon data in the fourth measurement interval 310 may not be reliable. The tamper datum 340 may also help explain changes in the radon data in the fourth measurement interval 310.

Figure 4:
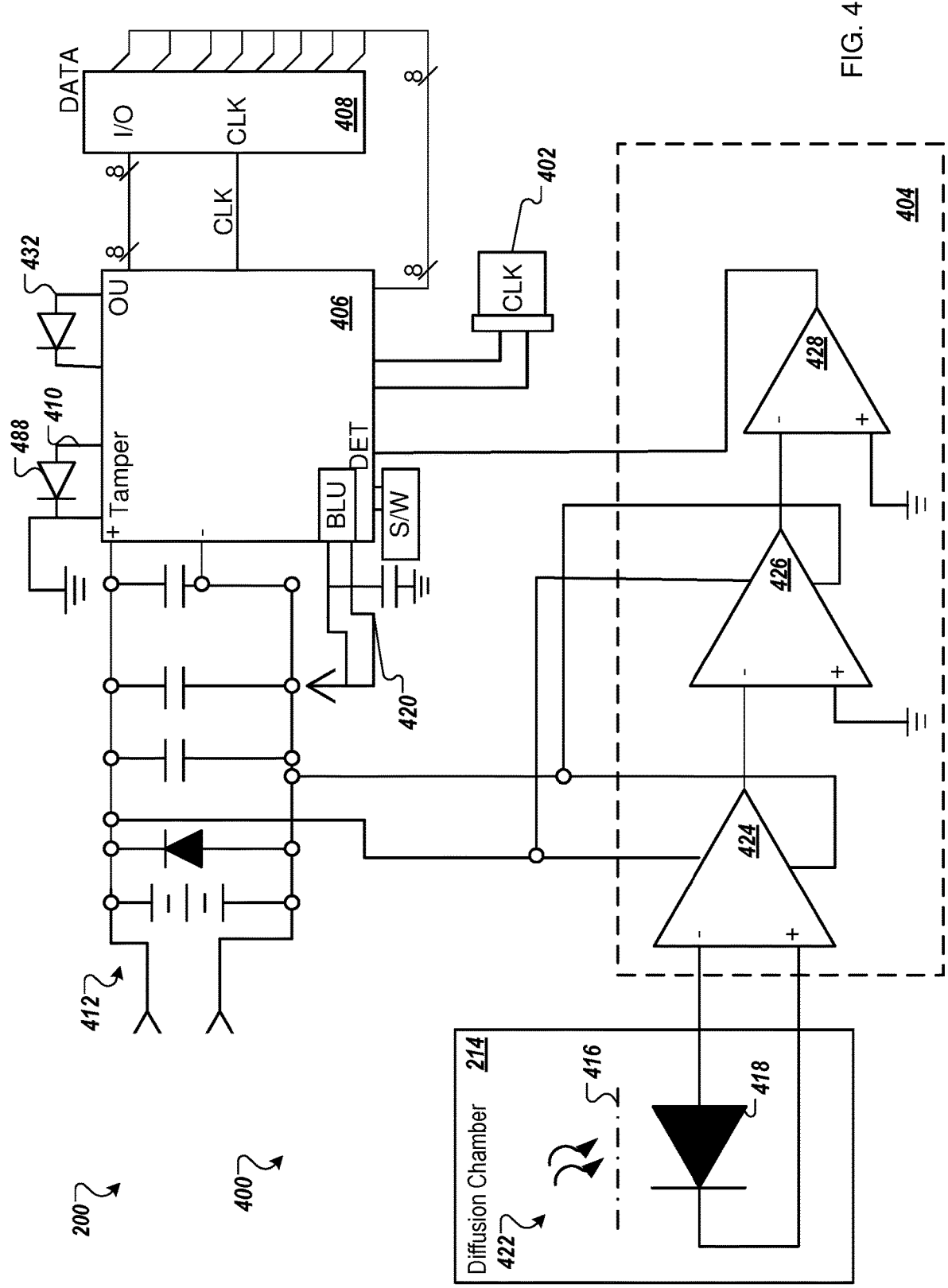
FIG. 4 illustrates an example electrical schematic that may be representative of an example embodiment of the device.

FIG. 4 illustrates an example electrical schematic 400 that may be representative of an example embodiment of the device 200. The schematic 400 includes the diffusion chamber 214. The diffusion chamber 214 includes a photodiode 418 that is configured to receive light 422 that occurs as radon decays. In the depicted embodiment, the light 422 may propagate through a screen 416 before impinging on the photodiode 418. The photodiode 418 is an example of the diffusion chamber sensor 212 described elsewhere in the present disclosure. The photodiode 418 may generate an electric signal that results from the light 422 impinging on the photodiode 418. The electrical signal may be communicated through an amplifier subassembly 404. In the depicted amplifier subassembly 404, there are three amplifiers 424, 426, and 428. In other embodiments, other arrangements of amplifier and amplifier circuits may be implemented. The amplifier subassembly 404 may be configured to output data that is representative of the light 422 detected by the photodiode 418.

The schematic 400 includes a power source 412, an antenna 420, a diode 432, a clock 402, a memory 408, a tamper detection mechanism 410, and measurement circuitry 406. Each of the power source 412, the antenna 420, the diode 432, the clock 402, the memory 408, and the measurement circuitry 406 may correspond to and/or be an example of a device component described elsewhere in the present disclosure.

The power source 412 may include a battery, a protector diode, and one or more capacitors. The one or more capacitors may perform power filter functions. The power source 412 may supply power to the other components included in the device 200. The power source 412 may correspond to the power source 210. In some embodiments, a voltage supplied by the power source 412 may be about 3.2 volts or another suitable voltage.

The antenna 420 may include a BLUETOOTH® antenna configured to pair and communicate data using one or more BLUETOOTH communication protocols. The antenna 420 may correspond to the information output 216 of FIGS. 1-2B. In other embodiments, the information output may include an access port as described elsewhere in the present disclosure. The antenna 420 may also include another type of antenna configured for wireless communication (e.g., WiFi, ZigBee, etc.). The antenna 420 may interface with the measurement circuitry 406 and/or the memory 408 to enable access to detection data sets that include data representative of the light 422 detected by the photodiode 418.

The diode 432 may be an example of the functional indicator 232. The diode 432 may change state based on measurement interval and/or tamper data. The measurement circuitry 406 may communicate a signal that supplies power at a frequency that results in the state of the diode 432. In some embodiments, the device 200 may include another type of functional indicator such as an audible alarm, a set of light emitting diodes, a vibrator, etc.

The clock 402 may correspond to the clock circuit 208 of FIG. 2B. An example of the clock 402 may include an X-TAL circuit or another suitable clock circuit. The clock 402 may output a clock signal. The clock signal is represented by "CLK" in FIG. 4.

The tamper detection mechanism 410 may include a photodiode 488. The photodiode 488 may be configured to receive light responsive to physical movement of the device 200. An electrical signal may be generated by the tamper detection mechanism 410 and communicated to the measurement circuitry 406. The electrical signal may be representative of tamper data. The tamper data may be communicated to the memory 408 along with a timestamp that is based on the clock signal.

The memory 408 may correspond to the storage medium 202. The memory 408 may include input/output pins and a clock pin. The input/output pins may receive data representative of the detected light 422. The clock pin may receive a clock signal from the clock 402. The memory 408 may be eight bit or sixteen bit. The memory 408 may store and/or enable access to the detection data sets, which may be communicated or otherwise made available to the antenna 420 and measurement circuitry 406 for output as described elsewhere herein.

The schematic 400 includes measurement circuitry 406. The measurement circuitry 406 may correspond to the measurement circuitry 206. The measurement circuitry 406 may be configured to receive the clock signal "CLK" and detect electrical signals from the amplifier subassembly 404. The measurement circuitry 406 may communicate a data signal that is representative of the detected light 422 to the memory 408. The measurement circuitry 406 may enable access to detection data sets stored on the memory 408 via the antenna 420.

Figure 5A:
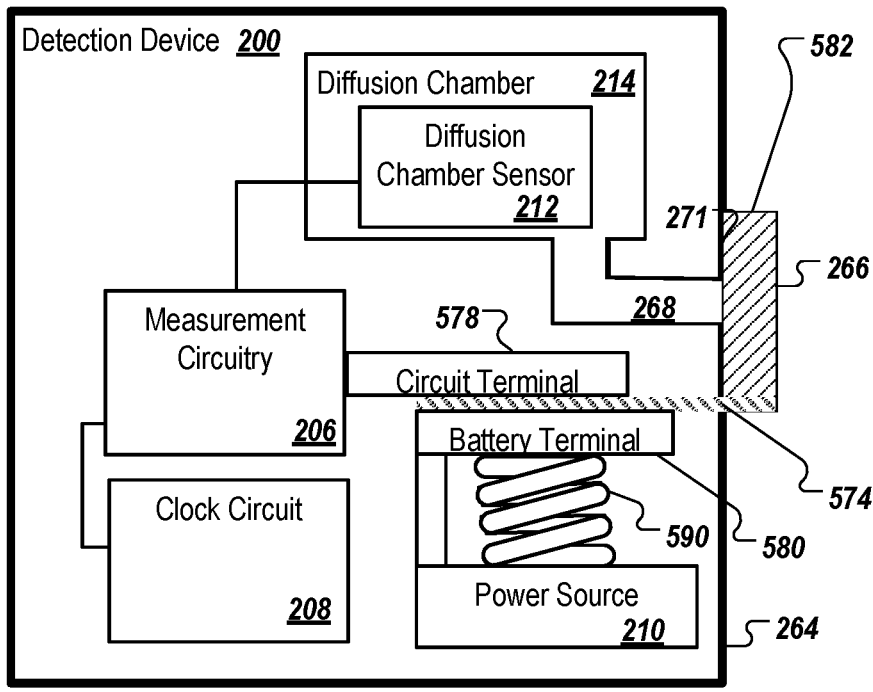
FIG. 5A illustrates a first example embodiment of the device in a pre-deployed configuration.
Figure 5B:
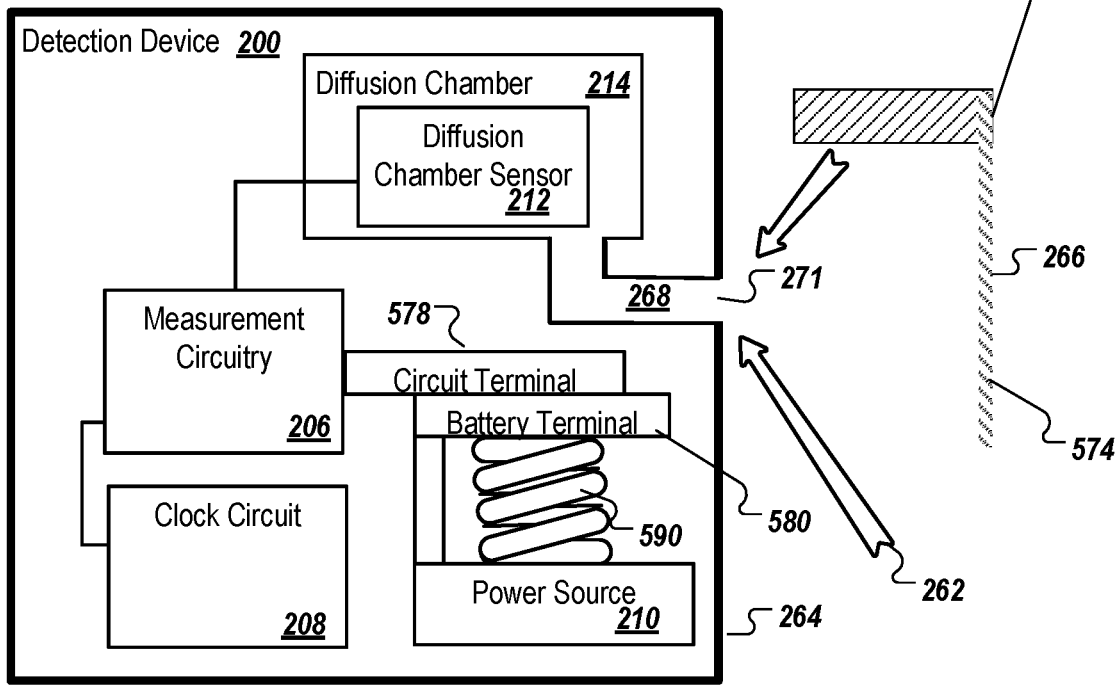
FIG. 5B illustrates the first example embodiment of the device in a deployed configuration.

FIGS. 5A and 5B depict an example embodiment of the device 200 according to at least one embodiment described in the present disclosure. FIG. 5A depicts the device 200 in a pre-deployed configuration. In the pre-deployed configuration the housing 264 may be substantially sealed by the triggering mechanism 266. In addition, in the pre-deployed configuration, the device 200 is laboratory calibrated. Accordingly, the diffusion chamber 214 and/or the diffusion chamber sensor 212 may be vacant. In the embodiment of FIGS. 5A and 5B, the first feature of the triggering mechanism 266 may include a vent cover 582. The vent cover 582 may be positioned over the vent 271. Thus, the vent cover 582 may isolate the diffusion pathway 268 from an ambient environment that surrounds the device 200.

The second feature of the triggering mechanism 266 may include an electrical insulator 574. The electrical insulator 574 may be integrally formed with the vent cover 582 or may be otherwise attached thereto. In the pre-deployment configuration (e.g., prior to the triggering action) the electrical insulator may be positioned between the power source 210 and the measurement circuitry 206. For instance, in the depicted embodiment, the measurement circuitry 206 may include a circuit terminal 578 and the power sources 210 may include a battery terminal 580. The electrical insulator 574 may be positioned between the circuit terminal 578 and the battery terminal 580. In some embodiments, a spring 590 may apply a force to press the battery terminal 580 against the electrical insulator 574 and the circuit terminal 578.

Thus, in the pre-deployed configuration, the vent cover 582 covers the vent 271 such that the diffusion pathway 268 is isolated from the surrounding environment and the measurement circuitry 206 is electrically isolated from the power source 210.

Referring to FIG. 5B, a deployed configuration of the device 200 is depicted. In the deployed configuration, the triggering mechanism 266 is removed from the device 200. Removal of the triggering mechanism 266 opens the vent 271 and removes the electrical insulator 574 from between the battery terminal 580 and the circuit terminal 578. In embodiments that include the spring 590, the battery terminal 580 may be forced into contact with the circuit terminal 578, which may enable supply of power to the measurement circuitry 206.

Accordingly, in the embodiment of FIGS. 5A and 5B, the triggering action may include the removal of the triggering mechanism 266. The triggering action may concurrently open the vent 271 and electrically trigger or initiate functionality of the measurement circuitry 206.

In the depicted embodiment is only one example embodiment in which the triggering mechanism 266 includes the vent cover 582 and the electrical insulator 574. In other embodiments, the electrical insulator 574 may be positioned between other terminals, or may otherwise electrically isolate the power source 210 or another electrical component (e.g., a ground, a control mechanism, etc.) from the measurement circuitry 206.

Figure 6A:
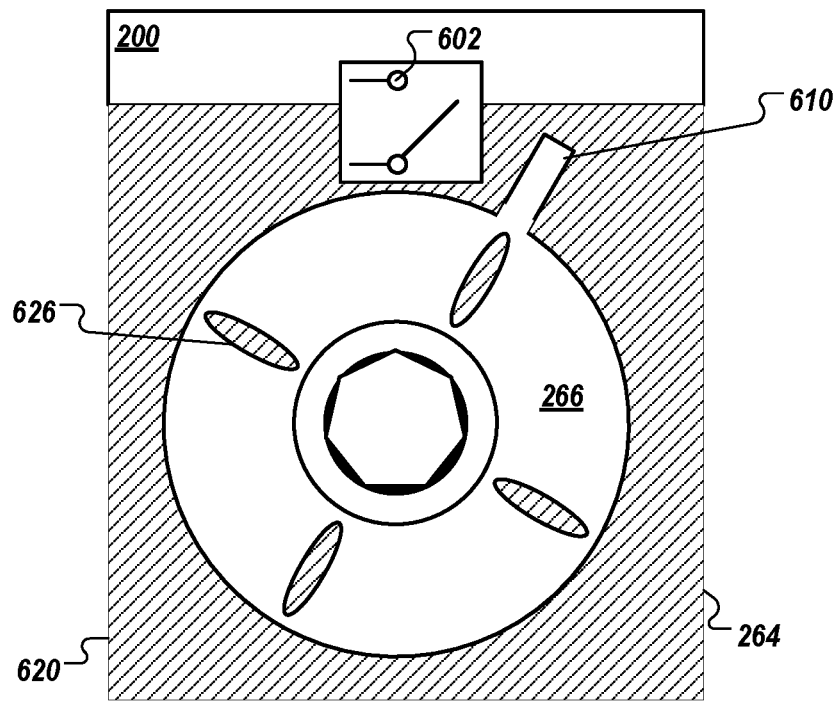
FIG. 6A illustrates a second example embodiment of the device in a pre-deployed configuration.
Figure 6B:
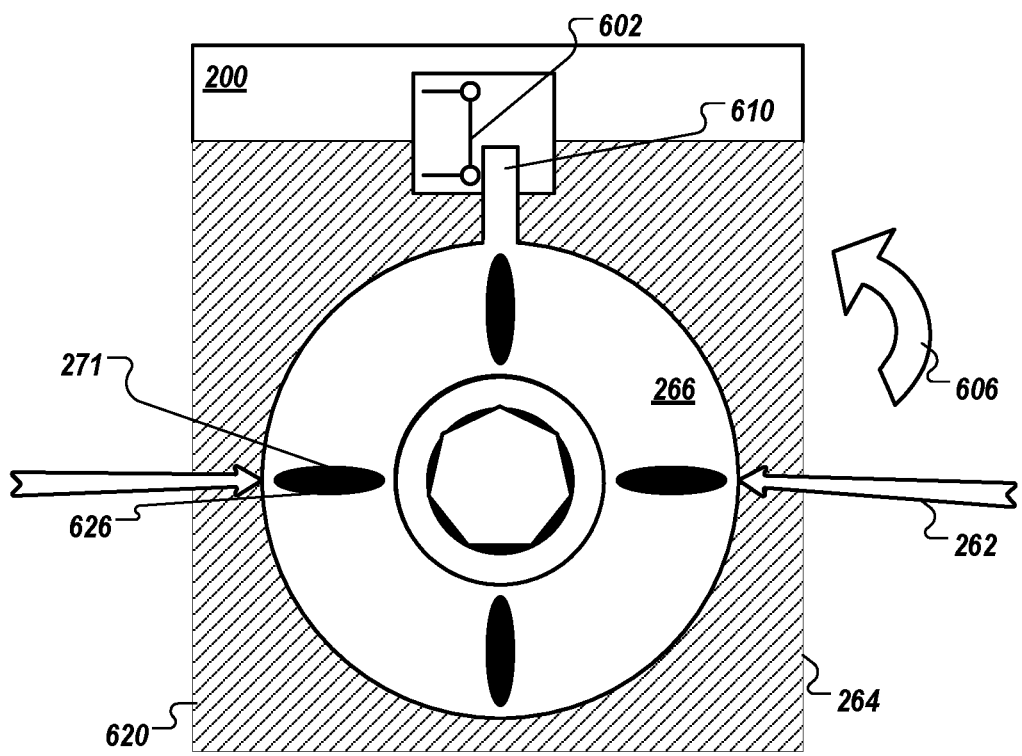
FIG. 6B illustrates the second example embodiment of the device in a deployed configuration.

FIGS. 6A and 6B depict block diagrams of another example embodiment of the device 200 according to at least one embodiment described in the present disclosure. FIGS. 6A and 6B depict an outer view of the device 200. For instance, the view of FIGS. 6A and 6B may be a front view or a side view of the device 200. In the embodiment of FIGS. 6A and 6B, the second feature includes an electrical switch 602. The electrical switch 602 may be configured to selectively electrically isolate a measurement circuitry (e.g., 206) from a power source (e.g., 210).

Additionally, the housing 264 may define vents 271 (FIG. 6B) in an outer housing surface 620. The vents 271 may include a shape that substantially corresponds to vent openings 626 defined in the triggering mechanism 266. The vent openings 626 may be the first feature of triggering mechanism 266. Additionally, the triggering mechanism 266 may include a protrusion 610. The protrusion 610 may be a part of the triggering mechanism that may be positioned relative to the electrical switch 602 such that motion of the triggering mechanism 266 actuates the electrical switch 602 by the protrusion 610.

FIG. 6A depicts the device 200 in a pre-deployed configuration. In the pre-deployed configuration the housing 264 may be substantially sealed by the triggering mechanism 266. For instance, the vent openings 626 are misaligned with the vent 271 and the electrical switch 602 is in an open position such that the vents 271 are sealed and the measurement circuitry is electrically isolated from the power source. In the pre-deployed configuration, the device 200 may be laboratory calibrated.

Thus, in the pre-deployed configuration, the portion of the triggering mechanism 266 between the vent openings 626 cover the vents 271 such that a diffusion pathway (e.g., 268) is isolated from an ambient environment. Additionally, because the electrical switch 602 is in an open state, the measurement circuitry is electrically isolated from the power source.

Referring to FIG. 5B, a deployed configuration of the device 200 is depicted. In the deployed configuration, the triggering mechanism 266 is rotated relative to the device 200. The rotation is represented in FIG. 5B by arrow 606. Rotation of the triggering mechanism 266 may align the vent openings 626 of the triggering mechanism 266 with the vents 271 defined in the outer housing surface 620. In addition, rotation of the triggering mechanism 266 may further rotate the protrusion 610 such that the protrusion 610 closes the electrical switch 602.

Accordingly, in the embodiment of FIGS. 6A and 6B, the triggering action may include rotation of the triggering mechanism 266 relative to the housing 264. The triggering action may concurrently open the vents 271 by aligning the vent openings 626 therewith and closing the electrical switch 602 such that functionality of the measurement circuitry is initiated.

In the depicted embodiment, there is only one example embodiment in which the triggering mechanism 266 includes the vent openings 626 and the protrusion 610. For example, the triggering mechanism 266 may be translated to align vent openings 626, or the triggering mechanism 266 may be pulled from the housing surface 620, or pushed into the housing surface 620.

Figure 7A:
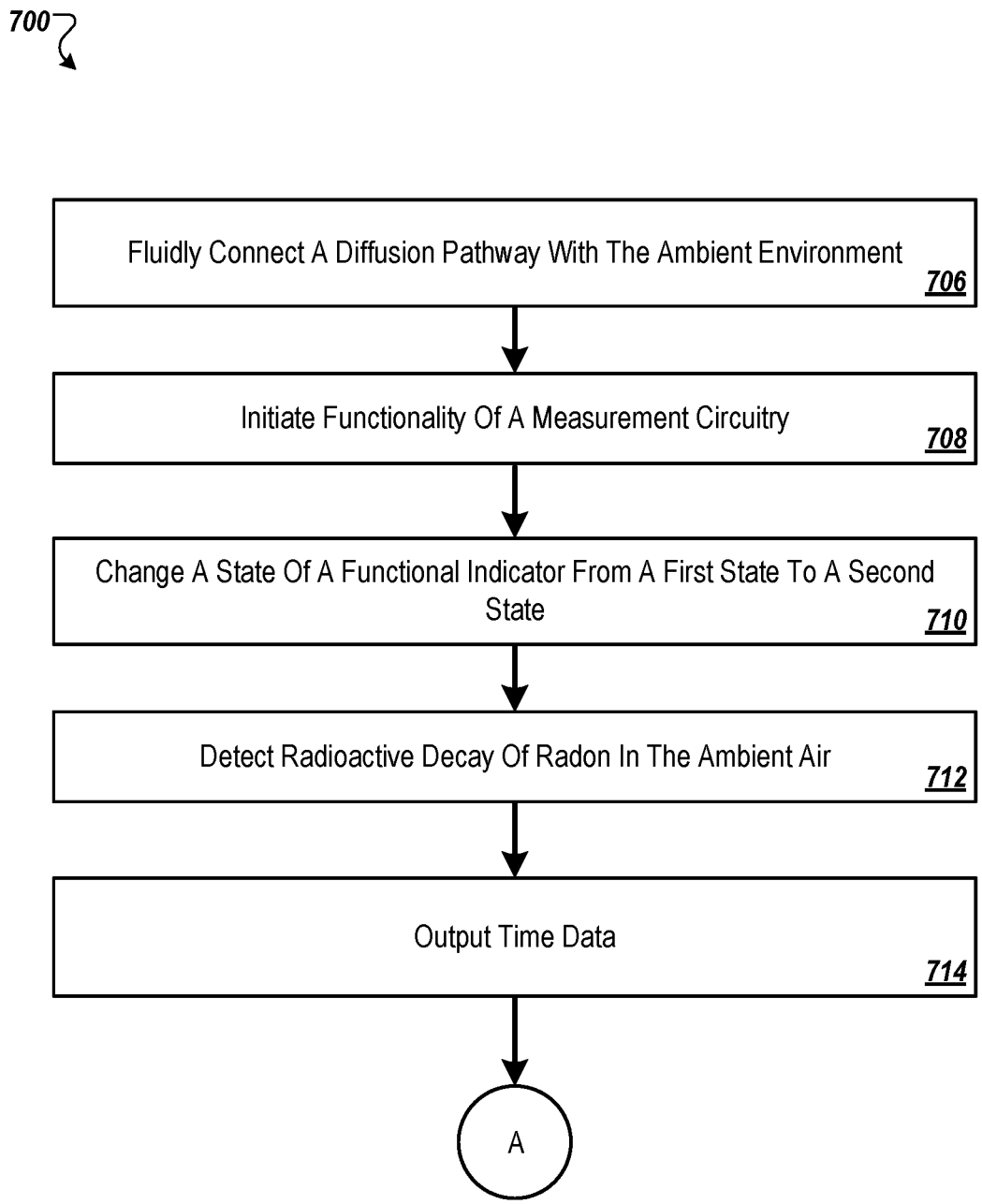
FIGS. 7A-7C are a flow chart of an example method of radon detection, all in accordance with at least one embodiment described in the present disclosure.
Figure 7B:
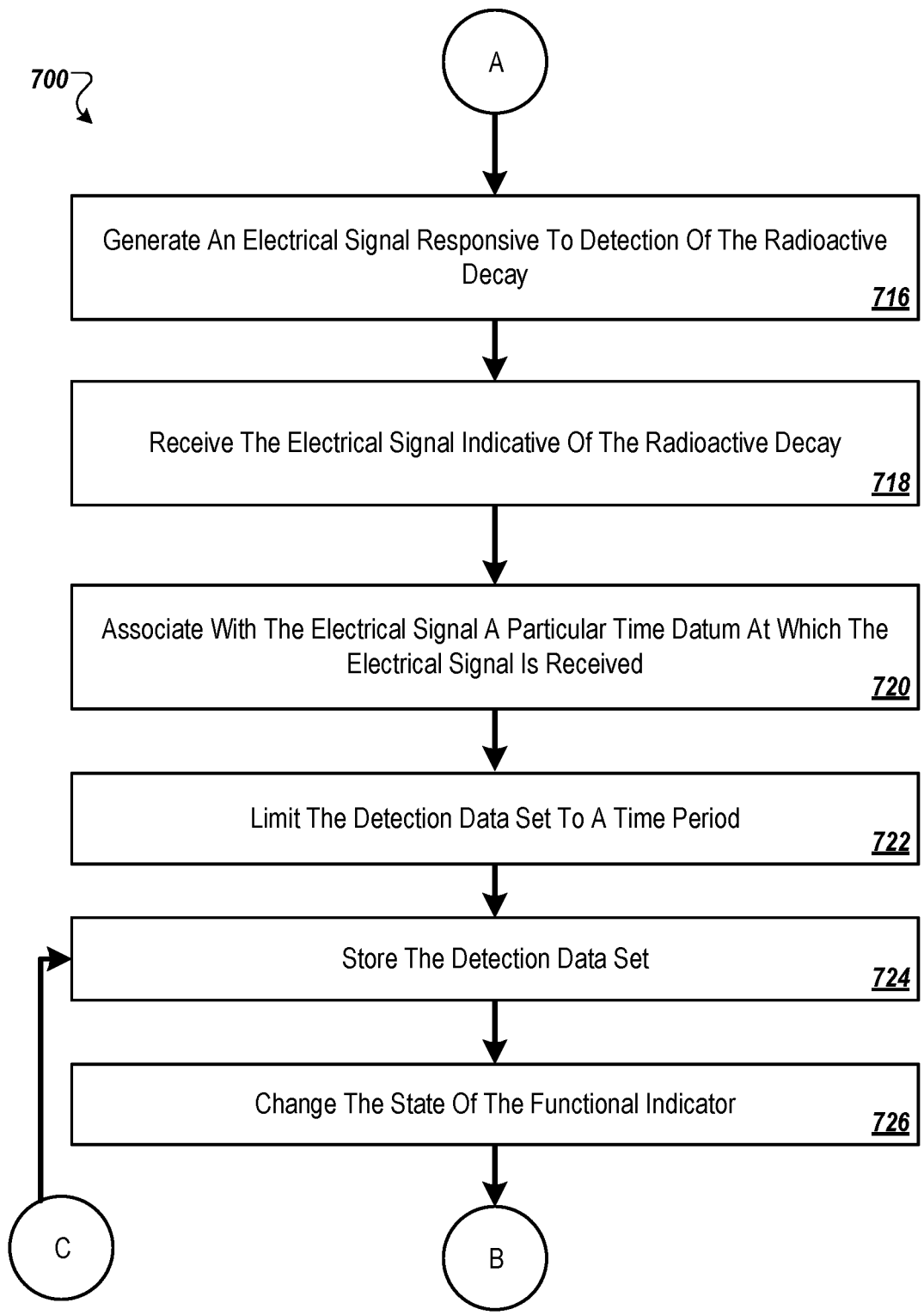
Figure 7C:
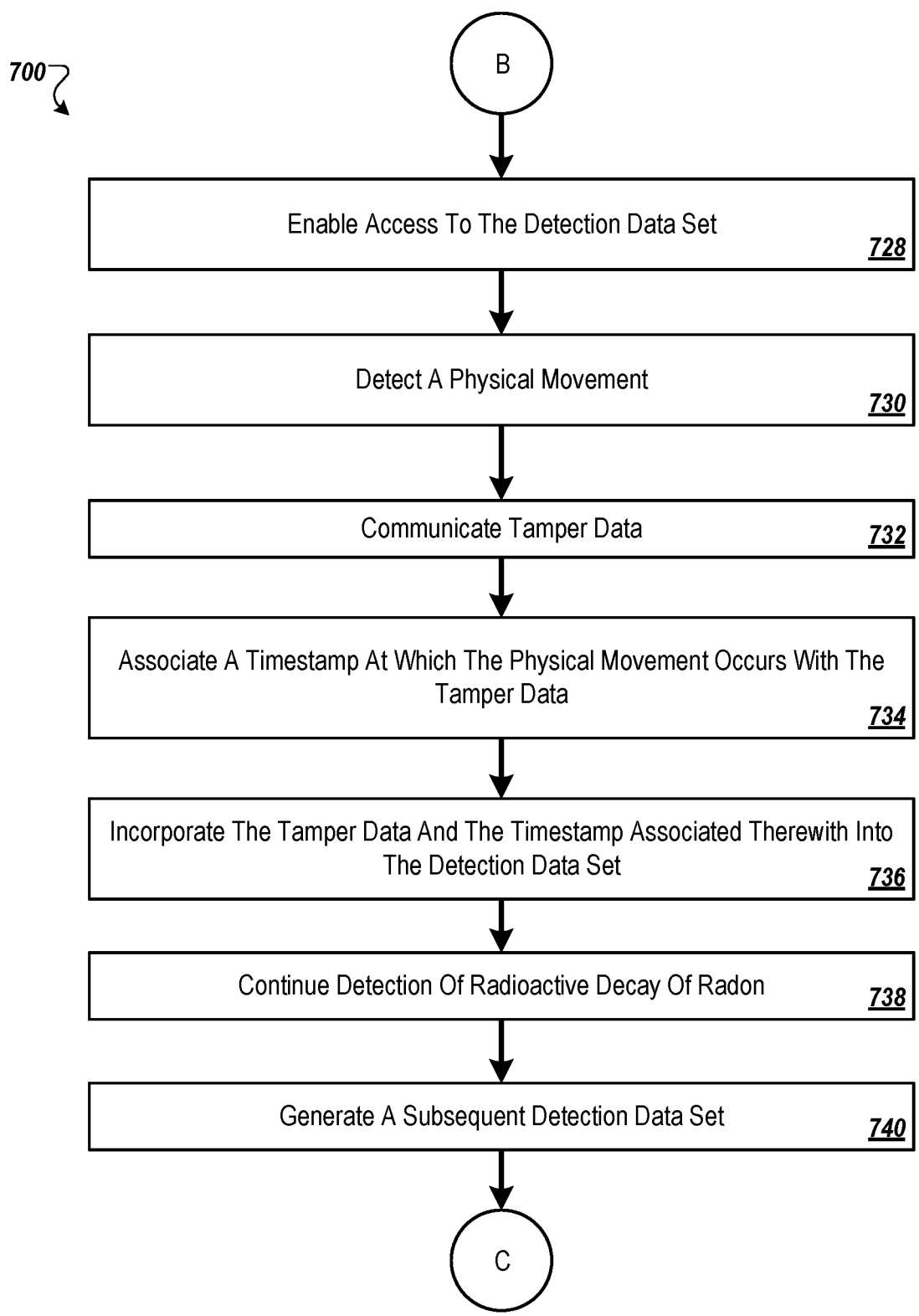

FIGS. 7A-7C are a flow chart of an example method 700 of radon detection, arranged in accordance with at least one embodiment described in the present disclosure. The method 700 may be implemented in a single use, single calibration device such as the device 200 described elsewhere in the present disclosure. Although illustrated as discrete blocks, various blocks may be divided into additional blocks, combined into fewer blocks, or eliminated, depending on the desired implementation.

The method 700 may begin at block 706, in which a diffusion pathway may be fluidly connected with an ambient environment. The diffusion pathway may be fluidly connected with the ambient environment via a vent that may be defined in a housing. The diffusion pathway may be fluidly connected with the ambient environment responsive to a triggering action that may be imposed on a triggering mechanism. The diffusion pathway may enable introduction of ambient air into a diffusion chamber coupled to a diffusion pathway and the vent. In some embodiments, the fluidly connecting the diffusion pathway with the ambient environment may include moving a vent cover relative to the vent. Movement of the vent cover relative to the vent may selectively isolate the diffusion pathway from the ambient environment.

At block 708, functionality of a measurement circuitry may be initiated. The functionality of the measurement circuitry may be responsive to the triggering action imposed on the triggering mechanism. Indeed, the fluidly connecting the diffusion pathway of block 706 and the initiating functionality of block 708 may occur concurrently or substantially concurrently. The initiating functionality of the measurement circuitry may include removing an electrical insulator that prior to the triggering action is positioned between a power source and the measurement circuitry. Additionally or alternatively, the initiating function of the measurement circuitry may include changing a state of an electrical switch that selectively electrically isolates the measurement circuitry from the power source. In some embodiments, the vent cover may define a vent opening and a protrusion positioned relative to the electrical switch. In these and other embodiments, the triggering action may include movement of the vent cover such that the vent opening is aligned with the vent. Concurrently with the movement of the vent cover, the protrusion may position the electrical switch to electrically couple the power source with the measurement circuitry. In some embodiments, prior to the triggering action, the vent cover may be positioned over the vent such that the diffusion pathway is isolated from the ambient environment. In these and other embodiments, the vent cover may be integrally formed with or otherwise mechanically coupled to the electrical insulator. The triggering action may accordingly include removal of the vent cover along with a second feature.

At block 710, a state of a functional indicator may change from a first state to a second state. The change of the functional indicator from the first state to the second state may be responsive to receipt of the triggering action. For instance, the functional indicator may include an LED, which may change from a first state of off to a second state of blinking amber. In other embodiments other states (e.g., changes in blinking, changes in color, multiple lights, audio alarms, mechanical changes, etc.) may be implemented.

At block 712, radioactive decay of radon may be detected. The decay of radon may be detected in the ambient air present in the diffusion chamber and/or the diffusion pathway. The radioactive decay may be detected by a diffusion chamber sensor positioned in the diffusion chamber within the housing. In some embodiments, the diffusion chamber sensor may include a photodiode, an amplifier, and a faraday chamber that protects the amplifier and the photodiode from electrostatic interference. In these and other embodiments, the diffusion chamber may be disposed in the housing and may include a casing that substantially prevents introduction of ambient light into the diffusion chamber.

At block 714, time data may be output. The time data may be output by a clock circuit. The time data may be output responsive to an initiation signal. The initiation signal may be generated responsive to the triggering action. With reference to FIG. 7B, at block 716, an electrical signal responsive to detection of the radioactive decay may be generated. For example, the diffusion chamber sensor may be configured to generate the electrical signal and communicate the electrical signal to the measurement circuitry. At block 718, the electrical signal may be received. For example, the electrical signal may be received at the measurement circuitry. The received electrical signal may be indicative of the radioactive decay from the diffusion chamber sensor.

At block 720, a particular time datum at which the electrical signal is received may be associated with the electrical signal. The time data and the electrical signal may be associated in a detection data set. At block 722, the detection data set may be limited to a time period. The time period may be between the triggering action and a particular measurement interval. The particular measurement interval may include forty-eight hours in some embodiments. In other embodiments, the particular measurement interval may be another suitable period of time such as twenty-four hours, thirty-six hours, etc.

At block 724, the detection data set may be stored. The detection data set may be stored upon expiration of the time period. The detection data set may be stored on a non-transitory storage medium, which may be positioned in the housing and communicatively coupled to the measurement circuitry. At block 726, the state of the functional indicator may be changed. The state of the functional indicator may be changed from the second state to a third state. The state of the functional indicator may be changed responsive to expiration of the particular measurement interval. For example, the second state of blinking amber may change to the third state of solid amber. As discussed above, other states (e.g., changes in blinking, changes in color, multiple lights, audio alarms, mechanical changes, etc.) may be implemented.

With reference to FIG. 7C, at block 728, access to the detection data set may be enabled. For instance, access to the detection data set may be enabled via an information output. The information output may include a removable non-transitory medium interface device or a wireless transmitter. Other information output devices may be implemented such as a wired interface, etc.

At block 730, a physical movement may be detected. The physical movement may be detected of the device relative to an initial placement location. The physical movement may be detected by a tamper detection mechanism. The tamper detection mechanism may include a switch, a sensor, or another suitable tamper detection mechanism. At block 732, tamper data indicative of the physical movement may be communicated to measurement circuitry.

At block 734, a timestamp at which the physical movement occurs may be associated with the tamper data. For instance, the measurement circuitry may be configured to associate the timestamp with the tamper data. At block 736, the tamper data and the timestamp associated therewith may be incorporated into the detection data set.

At block 738, detection of radioactive decay of radon in the ambient air may be continued. The detection of the radioactive decay may continue following the expiration of the particular measurement interval. For example, detection of the radioactive decay may continue following the expiration of the particular measurement interval for one or more subsequent measurement intervals.

At block 740, a subsequent detection data set may be generated. The subsequent detection data set may be generated based on the continued detection. One or more or each of the one or more subsequent detection data sets may span one of the subsequent measurement intervals. In some embodiments, the subsequent measurement intervals may include a first subsequent measurement interval that is seventy-two hours following the triggering action, a second subsequent measurement interval that is seven days following the triggering action, a third subsequent measurement interval that is 30 days following the triggering action, and a fourth subsequent measurement interval that is 90 days following the triggering action. In other embodiments other subsequent measurement intervals may be implemented. From block 740, the method 700 may proceed through one or more of blocks 724, 726, 728, 730, 732, 734, 736, and 740 for the one or more subsequent detection data sets.

One skilled in the art will appreciate that, for this and other procedures and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the disclosed embodiments.

Terms used in the present disclosure and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.). Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one," "one or more," "at least one of the following," and "one or more of the following" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B. Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

The scope of the present invention serves as a solution to the current problems in radon measurement technologies. Examples below are problems and solutions made by the one or more embodiments described in the present disclosure.

All examples and conditional language recited herein are intended for pedagogical objects to aid the reader in understanding the example embodiments and the concepts contributed by the inventor to furthering the art, and are to be construed as being without limitation to such specifically-recited examples and conditions.

What is claimed is:

1. A radon detection and measurement device that is configured to have a pre-deployment laboratory calibration and is configured for a single measurement interval, the device comprising:

a housing that defines an internal cavity and includes a vent;

a diffusion chamber disposed in the internal cavity, the diffusion chamber including a casing that substantially prevents introduction of ambient light into the diffusion chamber;

a diffusion chamber sensor positioned in the diffusion chamber, the diffusion chamber sensor being configured to detect radioactive decay of radon in the diffusion chamber and responsive to detection of the radioactive decay, the diffusion chamber sensor is configured to generate an electrical signal;

a diffusion pathway that is coupled between the diffusion chamber and the vent, the diffusion pathway being configured to enable introduction of ambient air into the diffusion chamber;

a clock circuit configured to output time data responsive to an initiation signal;

measurement circuitry communicatively coupled to the diffusion chamber sensor and the clock circuit, the measurement circuitry being configured to receive the electrical signal from the diffusion chamber sensor and to associate with the electrical signal a particular time datum that is based on the time data at which the electrical signal is received in a detection data set; and a triggering mechanism that includes:
  a first feature that selectively physically isolates the vent from an ambient environment; and
  an electrical insulator configured to selectively electrically trigger the measurement circuitry, wherein:
  the triggering mechanism is configured to respond to a triggering action by concurrently or substantially concurrently affecting the first feature and the electrical insulator such that the diffusion pathway is fluidly connected with the ambient environment via the vent and functionality of the measurement circuitry is initiated, and
  the measurement circuitry is configured to limit the detection data set to a time period between the triggering action and the measurement interval.

2. The device of claim 1, further comprising:
a non-transitory storage medium positioned in the housing and communicatively coupled to the measurement circuitry, wherein the detection data set is stored on the medium upon expiration of the time period; and
an information output coupled to the storage medium, the information output enabling access to the detection data set stored on the medium.

3. The device of claim 2, wherein:
the diffusion chamber sensor includes a photodiode, an amplifier, and a faraday chamber that protects the amplifier and the photodiode from electrostatic interference;
the particular measurement interval includes forty-eight hours following the triggering action; and
the information output includes a removable non-transitory medium device or a wireless transmitter.

4. The device of claim 1, further comprising a power source, wherein
the first feature includes a vent cover that moves relative to the vent to selectively isolate the diffusion pathway from the ambient environment.

5. The device of claim 4, wherein:
prior to the triggering action, the vent cover is positioned over the vent such that the diffusion pathway is isolated from the ambient environment;

the vent cover is integrally formed with the electrical insulator; and
the triggering action includes removal of the vent cover along with the electrical insulator.

6. The device of claim 1, further comprising a functional indicator that is configured to change from a first state to a second state responsive to the triggering action and to change from the second state to a third state responsive to expiration of the particular measurement interval.

7. The device of claim 6, wherein:
the measurement circuitry is further configured to continue detection of radioactive decay of radon in the ambient air following the expiration of the particular measurement interval for one or more subsequent measurement intervals, and to generate one or more subsequent detection data sets based on the continued detection, each of the one or more subsequent detection data sets spanning one of the subsequent measurement intervals;
the subsequent measurement intervals include a first subsequent measurement interval that is seventy-two hours following the triggering action, a second subsequent measurement interval that is seven days following the triggering action, a third subsequent measurement interval that is 30 days following the triggering action, a fourth subsequent measurement interval that is 90 days following the triggering action, and a fifth subsequent measurement interval that is one year following the triggering action; and
the functional indicator is further configured to change state to one or more subsequent states at the expiration of each of the subsequent measurement intervals.

8. The device of claim 1, further comprising tamper detection mechanism that is configured to detect a physical movement of the device relative to an initial placement location and to communicate tamper data indicative of the physical movement to measurement circuitry, wherein the measurement circuitry is configured to associate a timestamp at which the physical movement occurs with the tamper data.

9. The device of claim 8, wherein:
the tamper detection mechanism includes a gyroscopic sensor, a photodiode, or a switch that is physically actuated by the physical movement of the device; and
the timestamp of at which the physical movement occurs is indicated in the detection data set.

10. A method of radon detection in a calibration device that is configured to have a pre-deployment laboratory calibration and is configured for a single use, the method comprising:
responsive to a triggering action occurring, a triggering mechanism is configured to respond by:
  removing a first feature such that a diffusion pathway is fluidly connected with an ambient environment via a vent that is defined in a housing, the diffusion pathway enabling introduction of ambient air into a diffusion chamber coupled to the diffusion pathway and the vent, and
  removing an electrical insulator such that functionality of a measurement circuitry is initiated, wherein the fluidly connecting and the functionality of the measurement circuitry occur concurrently or substantially concurrently;
detecting, by a diffusion chamber sensor positioned in the diffusion chamber within the housing, radioactive decay of radon in the ambient air;
outputting time data responsive to an initiation signal;

generating an electrical signal responsive to detection of the radioactive decay;

receiving at the measurement circuitry the electrical signal from the diffusion chamber sensor;

associating with the electrical signal a particular time datum that is based on the time data at which the electrical signal is received in a detection data set; and limiting the detection data set to a time period between the triggering action and a particular measurement interval.

11. The method of claim 10, further comprising:

upon expiration of the time period, storing the detection data set on a non-transitory storage medium positioned in the housing and communicatively coupled to the measurement circuitry; and enabling access to the detection data set stored on the medium via an information output.

12. The method of claim 11, further comprising responsive to the triggering action occurring, changing a state of a functional indicator from a first state to a second state; and responsive to expiration of the particular measurement interval, changing the state of the functional indicator from the second state to a third state.

13. The method of claim 12, further comprising:

detecting a physical movement of the device relative to an initial placement location;

communicating tamper data indicative of the physical movement to measurement circuitry; and associating a timestamp at which the physical movement occurs with the tamper data.

14. The method of claim 13, further comprising incorporating the tamper data and the timestamp associated therewith into the detection data set.

15. The method of claim 14, wherein:

the diffusion chamber sensor includes a photodiode, an amplifier, and a faraday chamber that protects the amplifier and the photodiode from electrostatic interference;

the particular measurement interval includes forty-eight hours;

the diffusion chamber is disposed in the housing and includes a casing that substantially prevents introduction of ambient light into the diffusion chamber; and the information output includes a removable non-transitory medium interface device or a wireless transmitter.

16. The method of claim 10, wherein:

the fluidly connecting the diffusion pathway with the ambient environment via the vent includes a vent cover being moved relative to the vent to selectively isolate the diffusion pathway from the ambient environment.

17. The method of claim 10, wherein:

prior to the triggering action, the vent cover is positioned over the vent such that the diffusion pathway is isolated from the ambient environment;

the vent cover is integrally formed with the electrical insulator; and the triggering action includes removal of the vent cover along with the electrical insulator.

18. The method of claim 10, further comprising:

continuing detection of radioactive decay of radon in the ambient air following expiration of the particular measurement interval for one or more subsequent measurement intervals;

generating one or more subsequent detection data sets based on the continued detection, each of the one or more subsequent detection data sets spanning one of the subsequent measurement intervals; and changing a state of a functional indicator to one or more subsequent states at the expiration of each of the subsequent measurement intervals, wherein the subsequent measurement intervals include a first subsequent measurement interval that is seventy-two hours following the triggering action, a second subsequent measurement interval that is seven days following the triggering action, a third subsequent measurement interval that is 30 days following the triggering action, a fourth subsequent measurement interval that is 90 days following the triggering action, and a fifth subsequent measurement interval that is one year following the triggering action.

* * * * *